(12) United States Patent
Eckmiller

(10) Patent No.: US 7,447,548 B2
(45) Date of Patent: Nov. 4, 2008

(54) RETINAL IMPLANT WITH IMPROVED IMPLANTATION AND WORKING PROPERTIES

(75) Inventor: Rolf Eckmiller, Neuss (DE)

(73) Assignee: IMI Intelligent Medical Implants AG, Zug (CH)

( * ) Notice: Subject to any disclaimer, the term of this patent is extended or adjusted under 35 U.S.C. 154(b) by 686 days.

(21) Appl. No.: 11/087,745

(22) Filed: Mar. 24, 2005

(65) Prior Publication Data

US 2005/0251223 A1    Nov. 10, 2005

Related U.S. Application Data

(63) Continuation of application No. 10/056,208, filed on Jan. 28, 2002, now abandoned.

(30) Foreign Application Priority Data

Nov. 9, 2001   (DE) .................. 101 54 700

(51) Int. Cl.
*A61N 1/00* (2006.01)
(52) U.S. Cl. .......................... 607/54; 607/53
(58) Field of Classification Search .......... 607/53, 607/54, 88, 141
See application file for complete search history.

(56) References Cited

U.S. PATENT DOCUMENTS

| | | | |
|---|---|---|---|
| 4,628,933 A | 12/1986 | Michelson | |
| 5,935,155 A | 8/1999 | Humayun et al. | |
| 6,393,327 B1 | 5/2002 | Scribner | |
| 2002/0038134 A1 | 3/2002 | Greenberg et al. | |
| 2002/0198573 A1 | 12/2002 | Nisch et al. | |

FOREIGN PATENT DOCUMENTS

| | | |
|---|---|---|
| DE | 29 48 266 A | 5/1981 |
| DE | 199 31 083 C2 | 7/2002 |

OTHER PUBLICATIONS

M. Schwarz et al., "Hardware Architecture of a Neural Net Based Retina Implant for Patients Suffering from Retinitis Pigmentosa," Proc. IEEE Int'l Conf. on Neural Networks, Washington, DC, Jun. 3-6, 1996, pp. 653-658.
Eckmiller et al., "Retina Implant Projekt Jahresbericht 96/97," Oct. 6, 1997, pp. C-1 to C-5.
Leonhardt et al., "Electronic Design of a Phosphene Visual Prosthesis," Proc. San Diego Biomedical Symposium, XX, XX vol. 12, Jan. 31, 1973, pp. 247-259, XP00801117.

*Primary Examiner*—Carl Layno
*Assistant Examiner*—Brian T. Gedeon
(74) *Attorney, Agent, or Firm*—Foley & Lardner LLP

(57) ABSTRACT

A retinal implant has at least one functional unit positioned internally inside an eye and at least one functional unit positioned externally outside the eye and at least one functional unit positioned outside the eye, which are separably connected to one another via a signal path in a manner designed for signal or data transmission. The patient's residual vision which may still remain is preserved because the signal path extends through the sclera of the eye and does not incorporate the anterior eye section.

19 Claims, 2 Drawing Sheets

RETINAL IMPLANT WITH IMPROVED IMPLANTATION AND WORKING PROPERTIES

CROSS-REFERENCE TO RELATED APPLICATION

This application is related to U.S. patent application Ser. No. 10/056,208 filed Jan. 28, 2002, and draws priority from German Application No. 10154700.5, filed on Nov. 9, 2001, both of which are incorporated herein by reference in their entirety.

BACKGROUND OF THE INVENTION

The present invention relates to a retinal implant.

An implant according to the generic type is known from U.S. Pat. No. 5,935,155. This document proposes that a functional unit (IGF) positioned inside the vitreous chamber be connected to an externally positioned functional unit (EPF) via wireless coupling of two coils. The coil of the internal functional unit is in this case arranged in the lens behind the iris.

In addition to the surgical intervention on the vitreous body for implanting the functional unit (IGF) positioned inside the vitreous chamber, a second surgical intervention is necessary in the anterior eye section for implanting the coil or a second functional unit (AGF) positioned outside the vitreous chamber (especially in the lenticular capsule in place of the intraocular lens (IOL), which needs to be removed beforehand).

The second functional unit (AGF), which is implanted in the lenticular capsule and is provided, in particular, in the case of various retinal implants, is mechanically connected to the IGF via a microcable and, in currently available versions, cannot be temporarily separated and re-connected. Technical solutions for this are, however, available. This mechanical connection makes the surgical interventions significantly more difficult since, when implanting the AGF in the lenticular capsule envelope, it is also necessary to make an opening in the lenticular capsule wall and to transfer the IGF, with the microcable connection, through this opening into the vitreous chamber. This entails additional risk factors such as: mechanical destabilisation of the lenticular capsule envelope by the additional opening; mechanical stress on the implant components, including the microcable; lengthening of the implantation time; increase in the risk of future pathological tissue changes, which may make the implant function or further surgical interventions (such as e.g. re-explantation) difficult or impossible.

Positioning the AGF in the anterior eye segment significantly restricts optical access to the retina and to the IGF. This can have a detrimental effect both on the function of the implant system and on sight, as well as on the medical inspectability of the vitreous chamber.

Externally positioned functional units (EPF) located outside the body are positioned immediately in front of the eye, in the normal field of view of the eye, in place of a spectacle lens or a contact lens, and hence impede any partial sight which may still remain (e.g. in subjects with macular degeneration and remaining extrafoveal vision). As the signal processing effort rises, especially in the case of retinal implants, when the number of microcontacts increases, the mass and energy demand of the microelectronic components rises significantly, so that in this context a limit for intraocularly implantable functional units is rapidly reached and the desired functional quality of the implant is thereby substantially restricted.

SUMMARY OF THE INVENTION

It is therefore an object of the present invention to provide a retinal implant in which the connection between the internal functional unit IGF and at least one external functional unit (AGF, EPF) does not interrupt the optical path between the lens and the extrafoveal region of the retina, and in which this connection is wireless or can be mechanically separated during implantation.

This object is achieved by a retinal implant comprising at least one internal functional unit arranged for being disposed inside an eye; at least one external functional unit arranged for being disposed outside the eye; and a signal path designed for at least one of signal and data transmission that connects the at least one internal functional unit to the at least one external functional unit, the signal path comprising a separable transscleral signal-path segment between the internal and external functional units, and wherein the signal path between the internal and external functional units does not incorporate the anterior eye section, including the cornea and intraocular lens.

Because the signal path extends through the sclera of the eye, inside the eye socket bounded by the conjunctiva, the optical path from the lens to the retina outside the foveal region remains free. The separability of the signal path permits separate implantability of the component implanted inside the eye and the component implanted outside the eye in the eye socket.

BRIEF DESCRIPTION OF THE DRAWINGS

Two exemplary embodiments of the present invention will be described below with reference to the drawing, in which.

DETAILED DESCRIPTION OF VARIOUS EMBODIMENTS OF THE INVENTION

Figure 1:
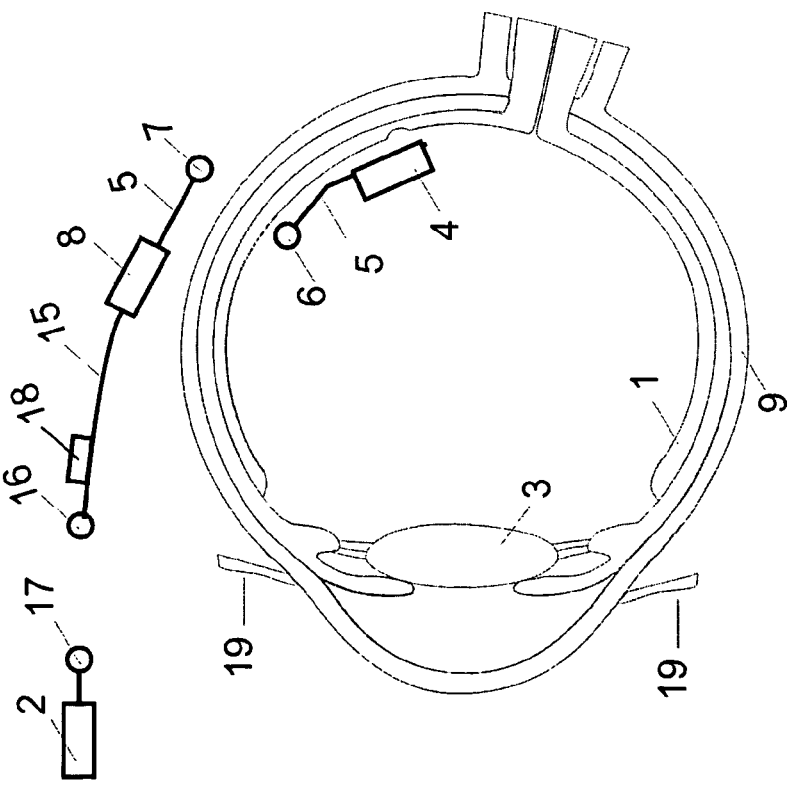
FIG. 1 shows an implant with a wireless inductive connection between the internal functional unit and a second functional unit implanted outside the eye.
Figure 3:
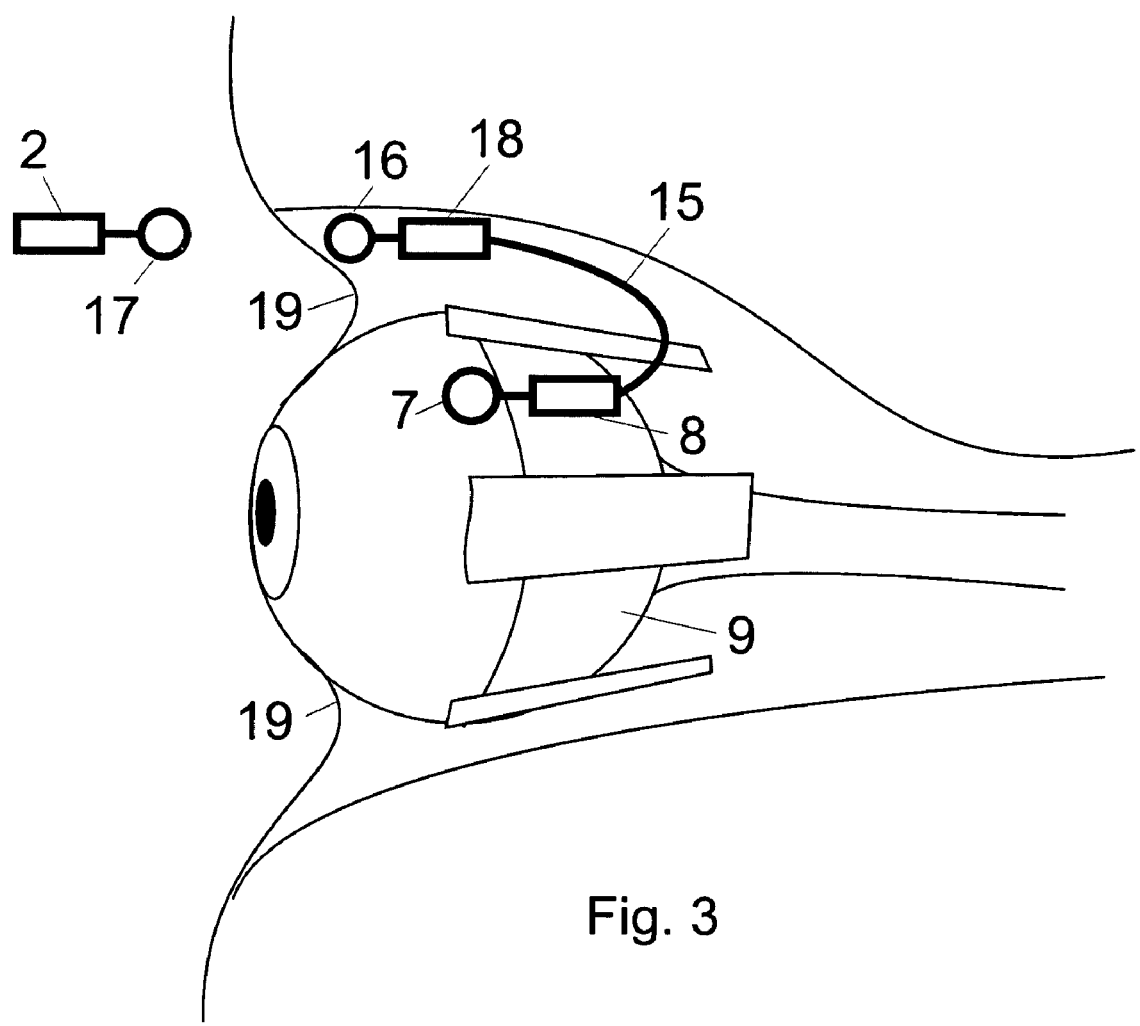
FIG. 3 shows a perspective representation of the implant according to FIG. 1.

FIG. 1 represents a retinal implant for patients having a degenerative disease of the retina 1, in which the functional unit(EPF) 2 present outside the body is positioned in the head region (e.g. on the side of a spectacle frame with normal spectacle function), in such a way that the optical beam path between viewed objects and the retina 1 is impaired neither by functional units directly in front of the eye nor by functional units in the anterior eye segment, including the intraocular lens (IOL) 3, and in such a way that, in particular, patients can thereby use their residual vision which may still remain (e.g. in the extrafoveal field of view in the case of macular degeneration), in addition to the implant function.

In a retinal implant according to the invention, the functional unit IGF 4 positioned inside the vitreous chamber is designed as a microcontact foil having associated microelectronics, a microcable S and at least one coil 6, and is fastened close to the retina in a suitable way. Via this coil 6 as part of the IGF 4 and at least one corresponding coil 7 as part of the AGF 8 inside the eye socket, a communication connection is made inductively through the sclera 9. Since the signal path through the sclera 9 of the eye extends inside the eye socket bounded by the conjunctiva 19, the optical path from the lens to the retina outside the foveal region remains free. The separability of the signal path permits separate implantability of the component implanted inside the eye and the component implanted outside the eye in the eye socket.

Figure 2:
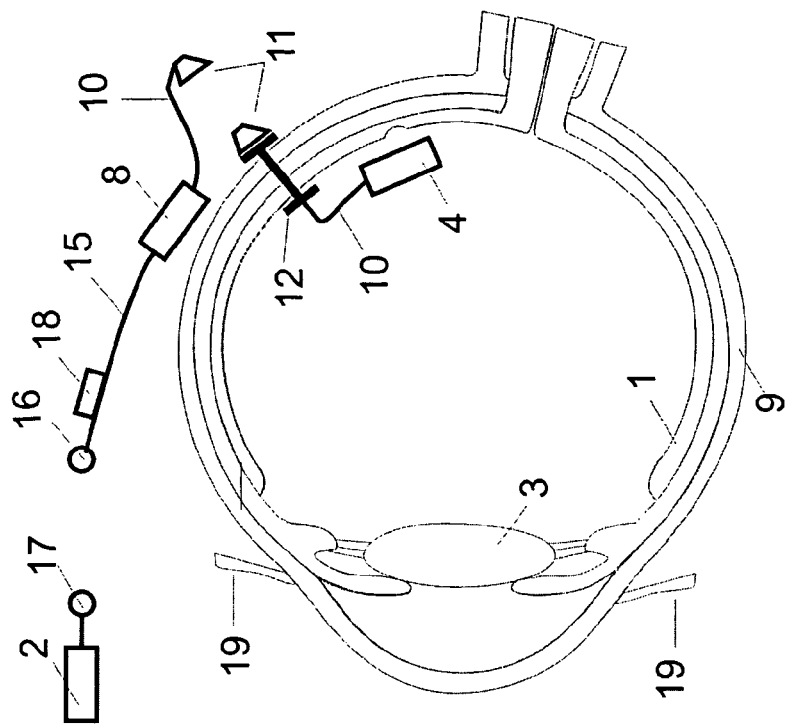
FIG. 2 shows a similar implant to FIG. 1, with a separable plug connection between the internal functional unit and a second functional unit implanted outside the eye.

FIG. 2 illustrates another embodiment of a retinal implant according to the invention. In this case, the transscleral connection between the IGF 4 and the AGF 8 is made galvanically via a microcable 10, this microcable being mechanically separated at a plug connection 11 during implantation, and the connection being made subsequently. Such a microcable connection 10 which can be made subsequently between the IGF 4, which e.g. performs only retinal stimulation, and an AGF 8 which undertakes decoder and/or demultiplexing functions, and which is implanted but located outside the eye, may preferably be configured in such a way that, according to the ophthalmological state of the art, a suitable transscleral cannula 12 is permanently implanted, the microcable 10 is fed through it, and the passage is sealed afterwards. The subsequent microcable connection 10 may furthermore be designed in such a way that the two ends to be galvanically connected (corresponding to a male or female plug connector) carry an equal number of complementarily shaped metal contacts (e.g. as pins at one cable end and as sockets at the other cable end) which, during the separate implantation of the IGF 4 and the AGF 8, are covered with an insulating thin plastic film for protection against the effect of fluids.

In a preferred embodiment, the microcable connection is established in that the pin part 11 and the socket part 11' are positioned flat facing one another while aligning the rows of pins and corresponding sockets, and in that the pin part and the socket part can thereupon be pressed cleanly against one another in such a way that, on the one hand, the insulating film is pierced and, on the other hand, securely insulated galvanic connections of the corresponding microcable lines 10 are made even under wet environment constraints.

In a preferred embodiment, this microcable connection can subsequently be re-separated by a suitable separating tool.

This separable microcable connection, consisting of the pin part 11 and the socket part 11', can preferably be produced both outside the eyeball in the eye socket (see FIG. 2) and inside the vitreous chamber (no image).

In likewise advantageous embodiments, the wireless transscleral communication is produced optoelectronically or by ultrasonic transmitter and receiver pairs on both sides of a circumscribed scleral zone.

In another embodiment, a cannula 12 is arranged in the wall of the sclera 9 according to the ophthalmological state of the art, and is shut off by a permeable film in the manner of a closed window.

In another embodiment, the AGF 8 is fastened sclerally to the outer wall of the bulb according to the ophthalmological state of the art (adhesive bonding, pinning or suturing) and has, in addition to a microcable 5 and at least one primary coil 7 fastened sclerally facing the respective corresponding coil 6 in the vitreous chamber, a further microcable 15 for connection to the functional unit (EPF) 2 located outside the body.

In a preferred embodiment, the connection between the AGF 8 in the eye socket and the external EPF 2 is made inductively via a coil pair 16, 17 and associated transmission and reception electronics 18, this coil pair 16, 17 being separated by a skin region in the head area (e.g. on the forehead) and the microcable 15 from the AGF 8 to the secondary coil 16 and the reception electronics 18 of this preferably transcutaneous inductive connection being laid under the skin according to the surgical state of the art.

In another possible version, the connection between the AGF 8 in the eye socket and the external EPF 2 is made via a suitable catheter structure and/or cable structure (not shown).

In an advantageous embodiment, in order to set up a function outside the normal implant operation, optical and/or optoelectronic communication is produced between a functional unit located outside the body and the IGF 4 in the vitreous chamber.

The external functional unit 2, which may comprise an encoder as well as camera means, may also, in one embodiment according to the invention, be worn by the patient in a manner other than with the conventional spectacle-type arrangement. For instance, the requisite components may also be arranged in a cap or a headband, which make it possible to avoid wearing spectacles which may be uncomfortably heavy. This furthermore permits the use of larger components, which are suitable for processing a larger number of optical channels or pixels.

I claim:

1. A retinal implant comprising:
   at least one internal functional unit arranged for being disposed inside an eye;
   at least one external functional unit arranged for being disposed outside the eye; and
   a signal path designed for at least one of signal and data transmission that connects the at least one internal functional unit to the at least one external functional unit, the signal path comprising a separable trans-scleral signal-path segment between the internal and external functional units, and wherein the signal path between the internal and external functional units does not incorporate the anterior eye section, including the cornea and intraocular lens, wherein the signal path comprises:
   an electrical cable; and
   a cannula, arranged for being inserted through the sclera, through which the electrical cable is fed.

2. The retinal implant according claim 1, wherein said at least one external functional unit comprises:
   a functional unit designed to carry out signal processing functions.

3. A retinal implant comprising:
   at least one internal functional unit arranged for being disposed inside an eye;
   at least one external functional unit arranged for being disposed outside the eye; and
   a signal path designed for at least one of signal and data transmission that connects the at least one internal functional unit to the at least one external functional unit, the signal path comprising a separable trans-scleral signal-path segment between the internal and external functional units, and wherein the signal path between the internal and external functional units does not incorporate the anterior eye section, including the cornea and intraocular lens, wherein said at least one external functional unit comprises:
   a first external functional unit for being disposed outside the eye socket; and
   a second external functional unit for being disposed within the eye socket but outside the eye, the second external functional unit being connected to the at least one internal functional unit by means of the signal path.

4. The retinal implant according to claim 3, wherein the signal path comprises a wireless inductive connection comprising:

at least one transmission element arranged for being disposed outside the eye; and at least one reception element arranged for being disposed inside the eye, wherein, when disposed outside and inside the eye, respectively, the at least one transmission element and at least one reception element are arranged facing one another, the sclera lying between the transmission and reception elements.

5. The retinal implant according to claim 3, wherein the signal path comprises a galvanic connection which passes through the sclera.

6. The retinal implant according to claim 5, wherein the galvanic connection comprises mutually complementary contact elements that are arranged for being connectable after implantation.

7. The retinal implant according to claim 6, wherein the mutually complementary contact elements are further arranged for being disconnectable after implantation.

8. The retinal implant according to claim 3, further comprising:

a second signal path for connecting the first external functional unit to the second external functional unit.

9. The retinal implant according to claim 8, wherein the second signal path comprises a wireless signal path.

10. The retinal implant according to claim 8, wherein the second signal path comprises:

a primary coil coupled to the first external functional unit; and a secondary coil coupled to the second external functional unit.

11. The retinal implant according to claim 8, wherein the second signal path comprises:

a reception circuit coupled to the second external functional unit, the reception circuit arranged for being disposed within the eye socket, the reception circuit receiving signals transmitted from the first external functional unit and passing them to the second external functional unit.

12. The retinal implant according to claim 8, wherein the second signal path comprises a catheter structure.

13. The retinal implant according to claim 8, wherein the second signal path comprises a cable structure.

14. A retinal implant comprising:

at least one internal functional unit arranged for being disposed inside an eye;

at least one external functional unit arranged for being disposed outside the eye; and a signal path designed for at least one of signal and data transmission that connects the at least one internal functional unit to the at least one external functional unit, the signal path comprising a separable trans-scleral signal-path segment between the internal and external functional units, and wherein the signal path between the internal and external functional units does not incorporate the anterior eye section, including the cornea and intraocular lens, wherein the signal path comprises an optical communication path.

15. The retinal implant according to claim 14, wherein said at least one external functional unit comprises:

a first external functional unit for being disposed outside the eye socket; and a second external functional unit for being disposed within the eye socket but outside the eye, the second external functional unit being connected to the at least one internal functional unit by means of the signal path.

16. The retinal implant according to claim 15, further comprising:

a second signal path for connecting the first external functional unit to the second external functional unit.

17. A retinal implant comprising:

at least one internal functional unit arranged for being disposed inside an eye;

at least one external functional unit arranged for being disposed outside the eye; and a signal path designed for at least one of signal and data transmission that connects the at least one internal functional unit to the at least one external functional unit, the signal path comprising a separable trans-scleral signal-path segment between the internal and external functional units, and wherein the signal path between the internal and external functional units does not incorporate the anterior eye section, including the cornea and intraocular lens, wherein the signal path comprises an optoelectronic communication path.

18. The retinal implant according to claim 17, wherein said at least one external functional unit comprises:

a first external functional unit for being disposed outside the eye socket; and a second external functional unit for being disposed within the eye socket but outside the eye, the second external functional unit being connected to the at least one internal functional unit by means of the signal path.

19. The retinal implant according to claim 18, further comprising:

a second signal path for connecting the first external functional unit to the second external functional unit.

* * * * *